(12) United States Patent
Kozyuk

(10) Patent No.: US 10,053,710 B2
(45) Date of Patent: Aug. 21, 2018

(54) METHOD FOR INCREASING ETHANOL YIELD FROM GRAIN

(71) Applicant: Arisdyne Systems, Inc., Cleveland, OH (US)

(72) Inventor: Oleg Kozyuk, North Ridgeville, OH (US)

(73) Assignee: ARISDYNE SYSTEMS, INC., Cleveland, OH (US)

( * ) Notice: Subject to any disclaimer, the term of this patent is extended or adjusted under 35 U.S.C. 154(b) by 811 days.

(21) Appl. No.: 13/916,008

(22) Filed: Jun. 12, 2013

(65) Prior Publication Data

US 2013/0273627 A1    Oct. 17, 2013

Related U.S. Application Data

(63) Continuation-in-part of application No. 12/961,597, filed on Dec. 7, 2010.

(60) Provisional application No. 61/267,900, filed on Dec. 9, 2009.

(51) Int. Cl.
- *C12P 7/06* (2006.01)
- *C12P 19/14* (2006.01)
- *C12N 13/00* (2006.01)

(52) U.S. Cl.
CPC ................ *C12P 7/06* (2013.01); *C12N 13/00* (2013.01); *C12P 19/14* (2013.01); *Y02E 50/17* (2013.01)

(58) Field of Classification Search
None
See application file for complete search history.

(56) References Cited

U.S. PATENT DOCUMENTS

| | | | |
|---|---|---|---|
| 5,931,771 A * | 8/1999 | Kozyuk | ............... 516/53 |
| 5,969,207 A | 10/1999 | Kozyuk | |
| 6,318,649 B1 | 11/2001 | Mazurkiewicz | |
| 6,857,774 B2 | 2/2005 | Kozyuk | |
| 7,101,691 B2 | 9/2006 | Kinley et al. | |
| 7,452,425 B1 | 11/2008 | Langhauser | |
| 7,667,082 B2 | 2/2010 | Kozyuk | |
| 8,143,460 B2 | 3/2012 | Kozyuk | |
| 2004/0028622 A1 | 2/2004 | Gurin | |
| 2008/0277264 A1 | 11/2008 | Sprague | |
| 2009/0186383 A1 | 7/2009 | Mancosky | |
| 2013/0273627 A1 | 10/2013 | Kozyuk | |
| 2014/0051141 A1 | 2/2014 | Kozyuk et al. | |

FOREIGN PATENT DOCUMENTS

WO    WO2008140997    11/2008

OTHER PUBLICATIONS

Souza et al., Evaluation of activity of a commercial amylase under ultrasound-assisted irradiation, Ultrasonics Sonochemistry, 20:89-94, Jun. 1, 2012.*

The International Search Report and Written Opinion issued in International PCT Application No. PCT/US2010/059164; dated Aug. 30, 2011.

* cited by examiner

*Primary Examiner* — Taeyoon Kim
*Assistant Examiner* — Srikanth Patury
(74) *Attorney, Agent, or Firm* — Pearne & Gordon LLP

(57) ABSTRACT

A process for increasing ethanol yield from grain that includes mixing grain, water and cavitated enzymes to form a grain-based liquid medium wherein the cavitated enzymes have increased activity and promote increased ethanol yield form the grain. The enzymes are passed individually through a cavitation apparatus at a velocity and pressure capable of generating a cavitation activation energy of at least 0.4 kJ per kilogram of liquid medium to enhance enzyme activity and increase ethanol yield.

5 Claims, 3 Drawing Sheets

METHOD FOR INCREASING ETHANOL YIELD FROM GRAIN

This application claims the benefit of U.S. provisional application Ser. No. 61/267,900 filed Dec. 9, 2009, and is a continuation-in-part of U.S. nonprovisional application Ser. No. 12/961,597 filed on Dec. 7, 2010, the contents of which are incorporated herein in their entirety by reference.

FIELD

The invention relates to processes for producing ethanol, and more particularly, processes for increasing ethanol yield using controlled cavitation to enhance enzyme activity.

BACKGROUND

Alcohols are a renewable and clean fuel source. A grain alcohol commonly used as a fuel source is ethanol, which can be produced, in large part, from corn by the fermentation of starch. Generally, ethanol production is accomplished through a fermentation and distillation process wherein starches are released and converted to sugars, and then the sugars are converted to alcohol by the addition of yeast. At an industrial level, yeast fermentation processes only convert about one-third of the corn into ethanol.

Ethanol production facilities often begin the production process with a dry or wet milling process. In dry milling, corn, or another suitable grain, is ground up by a hammer or roller mill into a dry mixture of particles. The dry mixture of particles is combined with water and enzymes to break up the starch from the corn into smaller fragments and then subject the smaller fragments to a saccharification phase wherein the starch is converted to sugar. After the saccharification phase, resulting sugars are fermented with yeast to facilitate their conversion to ethanol.

Ethanol yield is dependent upon initial starch content of the corn as well as the availability of the starch to the enzymes that are used in the saccharification phase. In conventional processes, the availability of starch is governed, in part, by the success of the dry milling or similar step in which the corn is broken up into smaller particles. Production processes currently used in commercial ethanol plants are not able to achieve maximum theoretical ethanol yield, thus more corn than theoretically needed must be used to produce a certain amount of ethanol.

In an attempt to increase ethanol yield, cavitation has been used; however, it has been limited to reducing particle size of the feed material for the purposes of enhancing subsequent treatment and providing more surface area for enzymatic breakdown of the starches to take place. Additionally, to achieve good particle size reduction, cavitational forces apply aggressive, shear stresses to the grain particles. If the cavitational forces apply too aggressive a shear force in terms of intensity, energy and/or duration, it is possible to cause damage to the components being treated. For example, a significant decrease in the particle size could have an adverse affect on downstream processing steps.

Also, aggressive cavitational forces can degrade desirable proteins and inactivate the enzymes. By collapsing hydrodynamic cavitation bubbles formed under specific conditions, extremely high local pressures and temperatures can be generated, which can promote enzyme denaturation. Cavitation can also promote chemical reactions involving H. and OH. free radicals formed by decomposing water inside the collapsing hydrodynamic cavitation bubbles. These free radicals could be scavenged by some amino acid residues of the enzymes participating in structure stability, substrate binding, or catalytic functions.

Accordingly, there is still a need for a process that can obtain a closer to theoretical maximum yield.

SUMMARY

A process of increasing ethanol yield in a starch-to-ethanol production process that includes passing enzymes through a controlled flow cavitation apparatus prior to distillation. The enzymes can be mixed with liquid prior to cavitation to form an enzyme stream free of grains.

A process for increasing ethanol yield from grain that includes the steps of passing a grain-based material with water through a first controlled flow cavitation apparatus to form a cavitated aqueous grain-based material slurry; passing enzymes through a second controlled flow cavitation apparatus to form a cavitated enzyme stream; and mixing the cavitated enzyme stream and the cavitated aqueous grain-based material slurry.

A process for increasing ethanol yield from grain that includes the steps of: mixing enzymes with water to form a pre-cavitated enzyme stream; subjecting the pre-cavitated enzyme stream to a cavitation activation energy not less than 0.4 kJ per kilogram of pre-cavitated enzyme stream to form a cavitated enzyme stream and enhance the activity of the enzymes; and mixing the cavitated enzyme stream with grain-based material.

DETAILED DESCRIPTION

Herein, when a range such as 5-25 (or 5 to 25) is given, this means preferably at least or more than 5 and, separately and independently, preferably not more than or less than 25. In an example, such a range defines independently not less than 5, and separately and independently, not more than 25.

To enhance enzyme activity in an ethanol production process, cavitational energy may be controlled to substantially increase ethanol yield from corn. Although an exact mechanism by which such cavitational energy enhances enzyme activity is unknown, there are several possible explanations. For example, forces obtained from cavitation are used to disaggregate, disassociate, shake off and/or strip away starch granules from protein, and fiber, as well as disassociate tightly packed granules and tightly packed amyloplasts containing starch granules to make them more accessible to an enzyme for subsequent enzymatic treatment. This increase in accessibility may increase enzyme activity in that the enzymes are more effective at breaking down grain as compared to an uncavitated enzyme. Cavitation energy may also enhance transportation of enzyme macromolecules toward a grain substrate's surface. In another example, absorption of cavitation energy by protein may produce a transient conformational shift (modifying the 3-dimensional structure) and alter the protein's functional activity to enhance its ability to liquefy grain at a faster rate as compared to uncavitated enzymes. In yet another example, cavitation bubbles will collapse and may contribute to an overall increase in the reaction rate, which can enhance removal of hydrolysis reaction products from a reaction zone.

Cavitation energy used to increase enzyme activity can be used at a dry grind ethanol production facility, a wet mill ethanol production facility, a dry grind and cellulous ethanol production facility, or a cellulose ethanol production facility.

Figure 1:
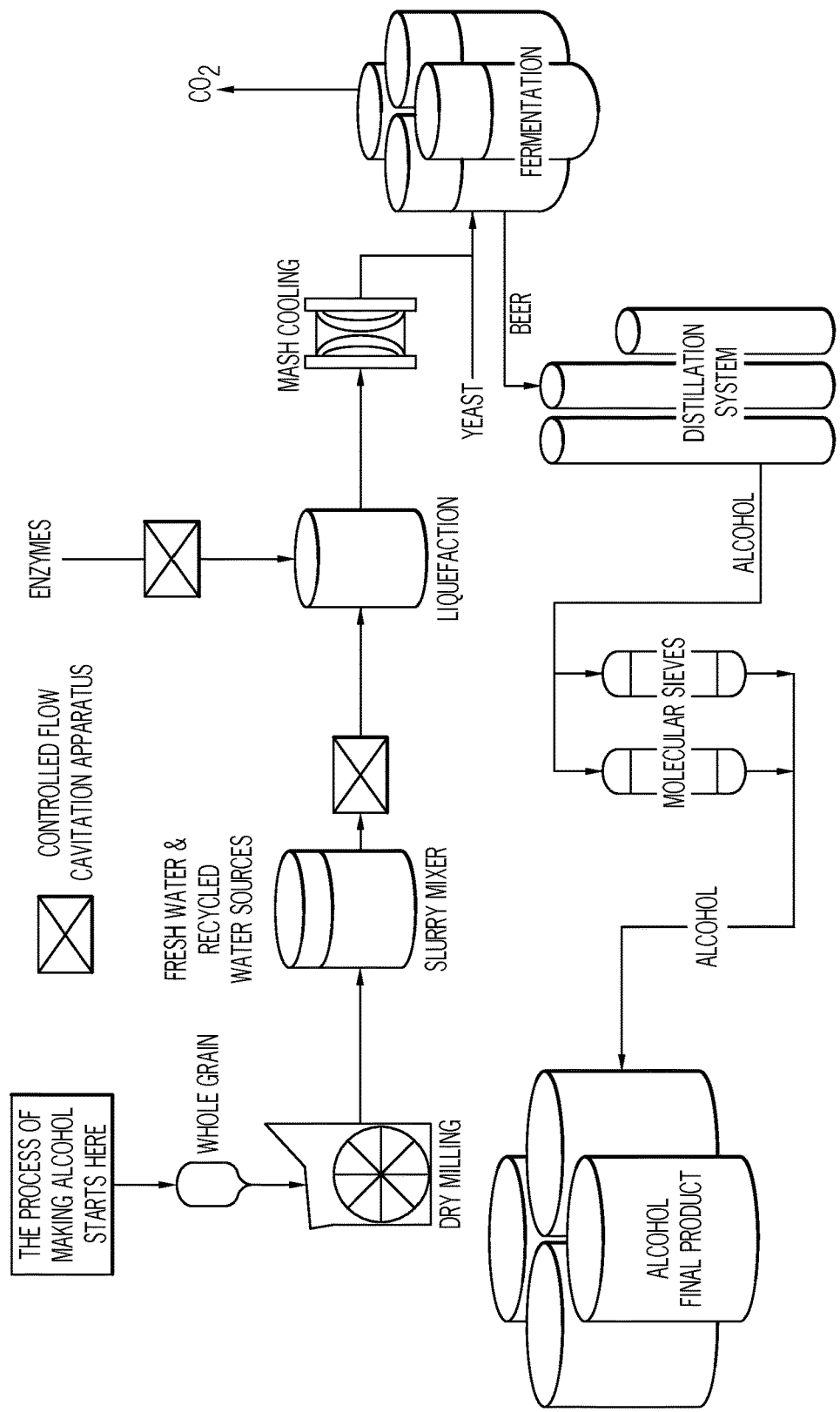
FIG. 1 is a flow diagram of an ethanol production process using cavitation.

Turning to the figures, FIG. 1. shows a starch to ethanol production process, wherein pipes, hoses, or other conventional industrial equipment can be used to facilitate the fluid communication of the elements and streams discussed herein. The production process begins when grain, such as whole kernel corn, is subject to a dry milling step. The dry milling step is used to grind the grain into meal or powder. For example, grains can include corn, rye, sorghum, wheat, beans, barley, oats, rice, or combinations thereof. As used herein, the term "grain" can comprise a whole grain or portions of the whole grain such as product from a dry-milling process used in an alcohol production process.

Next, grain-based material is mixed with water in a slurry mixer to form a pre-gelatinized grain-based liquid medium, which can be in the form of a slurry. The time in which the grain-based material and water are mixed together is preferably in the range of 15 to 60 minutes, for example at least 15, 20, 30, 40, 50 or 60 minutes. The temperature at which the mixing will take place is preferably in the range of 130 to 190° F., for example at least 130, 137, 140, 150, 160, 170, 180, 185 or 190° F.

As shown in FIG. 1, the pre-gelatinized grain-based liquid medium exits the slurry mixer and passes through a first controlled flow cavitation apparatus or device that is used to apply cavitational energy to the pre-gelatinized grain-based liquid medium and form a cavitated grain-based liquid medium. Prior to or during the liquefaction step, activation-enhanced cavitated enzymes can be added to the cavitated grain-based medium.

As shown, enzymes, preferably without any grain-based material present, can be passed through a second controlled flow cavitation apparatus to form a cavitated enzyme stream. Preferably, the enzymes are mixed with a liquid, such as water, to form a pre-cavitated liquid enzyme stream prior to being subjected to a specified cavitation activation energy in the second controlled flow cavitation apparatus. The pre-cavitated liquid enzyme stream can be free of grain and preferably contains less than 0.1, 0.5 or 1 weight percent of grain material based on the total weight of the pre-cavitated liquid enzyme stream. The pre-cavitated liquid enzyme stream can be passed through the second controlled flow cavitation apparatus at any desirable temperature, and preferably, for example, in the range of 20 to 100, 20 to 60 or 20 to 40° C. In one embodiment, the enzymes do not require pre-heating prior to cavitation and can be processed at room temperature to enhance their activity for increasing ethanol yield.

The cavitated enzyme stream can be added with cavitated grain-based medium in a liquefaction step as shown in FIG. 1. to form a cavitated enzyme-grain slurry. To further maximize production, the cavitated enzyme-grain slurry may pass through one or more additional controlled flow cavitation apparatuses prior to the liquefaction tank (not shown).

Figure 2:
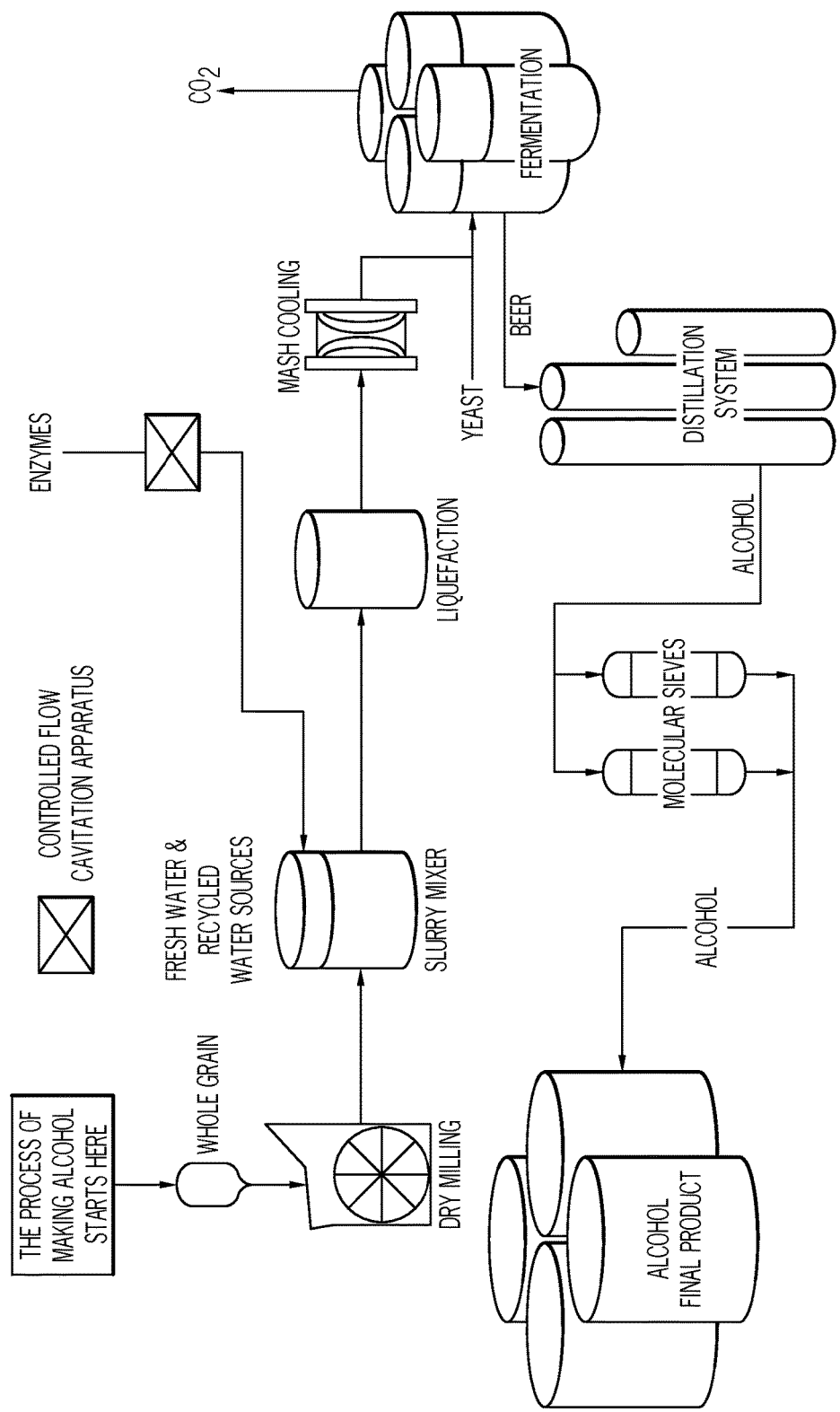
FIG. 2 is a flow diagram of an ethanol production process using cavitation.

Alternatively to mixing the cavitated grain-based medium and cavitated enzyme stream in the liquefaction step, the cavitated enzyme stream may be mixed with the cavitated aqueous grain-based material slurry to form a cavitated enzyme-grain slurry prior to the liquefaction step or after to the liquefaction step as shown in FIG. 2.

The activation-enhanced cavitated enzymes can be, but is not limited to, alpha-amylase, glucanase, beta-glucosidases, pectinases, xylanase, amylases, ligninases, proteases, beta-mannosidase, and similar enzymes, or a mixture thereof. In addition, the enzymes or a mixture of enzymes can be added at a concentration of 0.015 to 0.5 weight percent by weight of grain, such as corn, in the cavitated grain-based liquid medium, for example, enzymes can be added at a concentration of at least 0.015, 0.016, 0.2, 0.28, 0.3, 0.4 or 0.5 weight percent. For instance, as shown in the Example below, the enzymes can be alpha-amylase and can be present in the range of 0.16 to 0.40 weight percent by weight of corn grain in the cavitated grain-based liquid medium. The grain-based material in the cavitated grain-based liquid medium can be present at a concentration of 20 to 50 weight percent by weight of the pre-gelatinized grain-based liquid medium, for example, less than 50, 45, 40, 35, 30 or 25 weight percent. Preferably, the grain-based material is present at less than 35 weight percent.

The controlled flow cavitation apparatus that may be used to apply a specified cavitation activation energy to the pre-gelatinized grain-based liquid medium or enzymes sufficient to activate the enzymes and enhance their activity and ability to breakdown starches in the grain. Enzymes may be added into the grain-based material prior to applying cavitation activation energy, such as through the controlled cavitation apparatus, reduces the need for multiple enzyme additions and increases processing efficiency. Multiple processing steps prior to cavitation may not be needed, such as long periods of steeping with enzymes, grinding steps, etc.

FIG. 2 shows another embodiment of using cavitational energy to increase the activity of enzymes to increase ethanol yield. A pre-cavitated liquid enzyme stream can be passed through a controlled flow cavitation apparatus that delivers cavitational activation energy of 0.4 to 1.6 kJ per kilogram of enzymes to form a cavitated enzyme stream having enzymes with enhanced activity. The cavitated enzyme stream can be added to the slurry mixer containing the pre-gelatinized grain-based liquid medium to form a cavitated enzyme-grain slurry with cavitated enzymes. The cavitated enzyme stream can contain enough enzymes to create a concentration in the slurry mixer of 0.015 to 0.5 weight percent of enzyme per weight of grain. The pre-gelatinized grain-based liquid medium and cavitated enzymes can be passed to a liquefaction tank for further processing as described above. The cavitated enzyme stream has an enhanced activity that allows them to liquefy grain and breakdown starches at a faster rate as compared to uncavitated enzymes.

The cavitation activation energy as noted above should be applied at least at a level of about 0.4 kJ per kilogram of pre-gelatinized grain-based liquid medium or enzymes. Preferably, the cavitation activation energy is 0.4 to 1.6 kJ per kilogram of pre-gelatinized grain-based liquid medium or enzymes, for example at least 0.6, 0.8, 1, 1.2 or 1.4 kJ per kilogram. The temperature of the pre-gelatinized grain-based liquid medium or enzymes entering the controlled flow cavitation apparatuses can be in the range of 130 to 190° F., for example at least 140, 150, 160, 170 or 180° F. The pre-gelatinized grain-based liquid medium or enzymes exiting the controlled flow cavitation apparatuses can be passed through the controlled flow cavitation apparatuses only one time, or optionally recirculated back through the same controlled flow cavitation apparatuses as many times as desired.

Following the liquefaction step, the cavitated enzyme-grain slurry will then move on to a cooling phase, as shown in FIGS. 1 and 2, wherein the enzymes continue to break down the starch polymers of the grains into shorter sections of sugar and create a sugar mash. Once conversion to sugar mash is complete, the sugar mash will be transferred to fermentation containers or tanks wherein yeast will convert the sugars into carbon dioxide and alcohol, such as ethanol. Upon transfer of the sugar mash to the fermentation containers, additional enzymes, urea and yeast can be added to the sugar mash, which is left to ferment for a period of time, for example at least 60 hours. Resulting product from the fermentation containers is referred to as "beer" and contains alcohol and solids. These solids can be both soluble and insoluble, such as non-fermentable components left over from the grain. A distillation phase following the fermentation phase separates a liquid carrier, usually water, ethanol, and whole stillage from each other. The water can be recycled and used, for example, in the slurry tanks. The non-fermentable components are further separated in the distillation process, and can also be sold as high-protein animal feed.

Adding a cavitation step to the ethanol production process to enhance enzyme activity, wherein parameters such as pressure and temperature can be controlled, can increase ethanol yield. In general, cavitation can be described as the generation, subsequent growth and collapse of cavitation bubbles and cavities. During the collapse of the cavitation bubbles, high-localized pressures and temperatures are achieved. The cavitation bubbles contain mostly steam, although a level of steam fluctuates depending on a temperature at which the cavitation bubbles are formed. For instance, cavitation bubbles formed at lower temperatures contain less steam. Cavitation bubbles containing less steam will collapse more energetically and generate higher local temperatures and pressures. These higher temperatures and pressures can stimulate progress of various chemical reactions which may not be possible under ordinary conditions, such as standard temperature and pressure (STP). However, temperatures and pressures that are too high can have a deleterious effect on a reaction and promote enzyme denaturation. The processing and reaction conditions described below prevent undesirable reactions and minimize enzyme denaturation such that ethanol yield can be increased.

Figure 3:
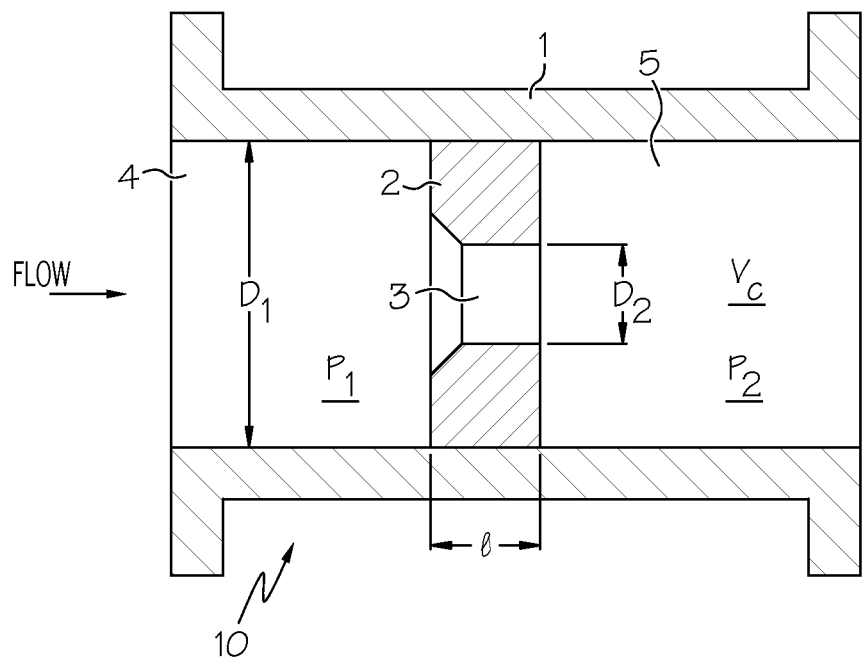
FIG. 3 is a cross section view of a controlled flow cavitation apparatus.

In one embodiment, FIG. 3 illustrates a controlled flow cavitation apparatus 10. FIG. 3 provides a cross section view of the controlled flow cavitation apparatus 10 which can process a grain-based liquid medium, such as a pre-gelatinized grain-based medium, or a pre-cavitated liquid enzyme stream. The controlled flow cavitation apparatus 10 comprises a flow-through channel 1 comprising a first chamber 4 and a second chamber 5. The first chamber 4 and second chamber 5 of the flow-through channel 1 are divided by a localized flow constriction 2. The first chamber 4 is positioned upstream of the localized flow constriction 2 and the second chamber 5 is positioned downstream of the localized flow constriction 2, as viewed in the direction of movement of flow, such as the grain-based liquid medium and pre-cavitated liquid enzyme stream. The second chamber 5 houses a hydrodynamic cavitation zone as discussed below. The hydrodynamic cavitation zone in the second chamber 5 has volume $V_c$. During operation, the first chamber 4 has static pressure $P_1$ and the second chamber 5 encompassing the hydrodynamic cavitation zone has static pressure $P_2$. Localized flow constriction can be achieved by a diaphragm with one, or more, orifices.

As shown in FIG. 3, the controlled flow cavitation apparatus 10 comprises one cylindrical orifice 3. The orifice 3 of the controlled flow cavitation apparatus 10 can be any shape, for example, cylindrical, conical, oval, right-angled, square, etc. Depending on the shape of the orifice 3, this determines the shape of the cavitation fluid jets flowing from the localized flow constriction 2. The orifice 3 can have any diameter, $D_2$, for example, the diameter can be greater than 0.1, 1, 2, 3, 5, or 10 mm, and preferably more than 3 mm. In one example, the diameter of the orifice 3 can be about 3 mm or about 4 mm.

As shown, the first chamber 4 has the static pressure pressure $P_1$ and the second chamber 5 has the static pressure $P_2$. Flow into the controlled flow cavitation apparatus 10 can be provided with fluid pumping devices as known in the art, such as a pump, centrifugal pump, positive-displacement pump or diaphragm pump. An auxiliary pump can provide flow under a static pressure $P_1$ to the first chamber 4. As discussed herein, pressure $P_1$ is defined as the processing pressure for the controlled flow cavitation apparatus 10. The processing pressure is preferably at least 30, 40, 50, 60, 70, 80, 90, 100, 120, 140, 150, 170, 200, 300, 400, 500, 600, 700, 800, 850, 900, or 1000, psi. The processing pressure is reduced as the pre-gelatinized grain-based liquid medium or pre-cavitated liquid enzyme stream passes through the flow-through channel 1 and orifice 3. Maintaining a pressure differential across the orifice 3 allows control of the cavitation intensity in the flow-through channel 1. The pressure differential across the orifice 3 is preferably at least 30, 40, 50, 60, 70, 80, 90, 100, 120, 140, 150, 170, 200, 300, 400, 500, 600, 700, 800, 850, 900, or 1000, psi. Velocity of the pre-gelatinized grain-based liquid medium or pre-cavitated liquid enzyme stream through the orifice 3 in the controlled flow cavitation apparatus 10 is preferably at least 1, 5, 10, 15, 20, 25, 30, 40, 50, 60 or 70 meters per second (m/s).

In the Example below, the controlled flow cavitation apparatus 10 described herein can be used as a single-pass process for enhancing the activity of the enzymes. Hydrodynamic cavitation arises in cavitation fluid jets flowing from the orifice 3 in the form of intermingling cavitation bubbles and separate cavitation cavities. That is, the orifice 3 creates the hydrodynamic cavitation zone that promotes a high density of cavitation power dissipation locally inside the flow-through channel 1, and more preferably in the orifice 3 chamber and downstream of the orifice 3 in the second chamber 5. The high energy dissipation in the hydrodynamic cavitation zone causes the cavitation activation energy for promoting the activity of the enzymes in the pre-cavitated liquid enzyme stream for increasing ethanol yield.

Dynamic pressure and residence time of cavitation bubbles or steam bubbles in the localized flow constriction 2 allow production of cavitation bubbles and cavitation cavities in liquid flow. The cavitation cavity sizes are dependent on the magnitude of a dynamic pressure jet as well as the sizes of orifice 3 in the localized flow constriction 2. Increase of the dynamic pressure jet as well as size of orifice 3 leads to an increased size of the cavitation bubbles. Increase of the dynamic pressure of the cavitation fluid jet also promotes an increased concentration of cavitation bubbles. Therefore, given the dynamic pressure of the cavitation fluid jet, its shape, and number of cavitation fluid jets, it is possible to produce a cavitation field or zone of cavitation bubbles in the downstream second chamber 5. Cavitation bubbles and cavitation cavities together with the cavitation fluid jets enter into the second chamber 5, where cavitation bubbles collapse under the influence of static pressure $P_2$. Energy emitted during collapse of the cavitation bubbles is directly proportional to magnitude of static pressure in surrounding liquid bubbles. Therefore, magnitude of $P_2$, is directly related to energy emitted during cavitation bubbles collapse and better dispersion and/or size reduction effect. In other words, energy dissipation in the grain-based fluid medium and enzymes increases as the magnitude of $P_2$ increases, and thus, severity or hardness of collapse of each cavitation bubble separately increases, as well as the energy dissipated due to the decrease of the volume in which these cavitation bubbles collapse.

As shown in the Example below, it has been found that cavitation generates specified cavitation activation energy for promoting activity of the enzymes. A specified range of cavitation activation energies preferably create hydrodynamic steam cavitation bubbles that collapse less energetically to avoid enzyme denaturation and deleterious effect on a reaction in the alcohol production process. Because cavitation bubbles containing less steam collapse more energetically and generate higher local temperatures and pressures, which can be undesirable, the specified cavitation activation energy, processing temperature, aqueous grain-based material slurry make up are believed to create steam-filled hydrodynamic cavitation bubbles that avoid these disadvantages.

The length (l) in orifice 3 in localized flow constriction 2 is selected in such a manner in order that the residence time of the cavitation bubbles. For example, the hydrodynamic steam cavitation bubble, in the orifice 3 and/or the second chamber 5 is less than 10 seconds, preferably less than 1 second or preferably less than 0.1 second. The time in the hydrodynamic cavitation zone that is needed to enhance and promote the enzyme activity is much smaller than known methods, such as ultrasonic or acoustic, and thus the controlled flow cavitation apparatus 10 can reduce processing time and costs associated with an alcohol production process. Because processing time directly relates to the amount of alcohol that can be produced, use of a controlled flow cavitation apparatus 10 can increase the yield of alcohol and reduce the amount of processing time required to produce the alcohol. Hydrodynamic cavitation is more efficient than acoustic cavitation and much more efficient than conventional agitation and/or heating methods. Further, scale-up of hydrodynamic cavitation apparatuses is relatively easy compared to other methods, which makes it well suited to the processing of dispersions and slurries, such as those present in an alcohol production process.

Figure 4:
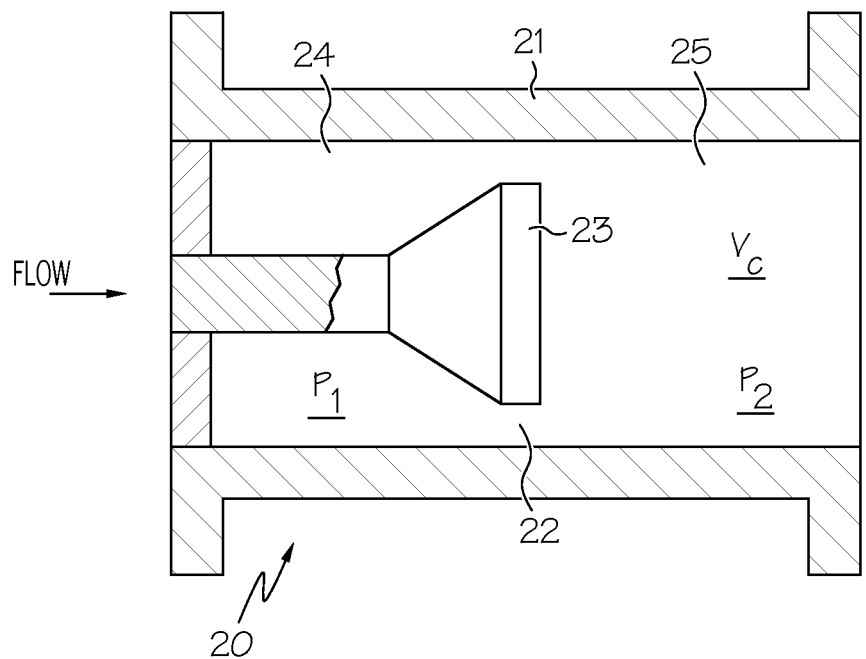
FIG. 4 is a cross section view of a controlled flow cavitation apparatus.

In another embodiment, FIG. 4 provides a cross section view of a cavitation apparatus 20. A bluff body 23 is positioned in the flow-through channel 21 to create localized flow constrictions 22, wherein two localized flow restrictions are created in parallel to one another. Each localized flow restriction positioned between the flow-through channel 21 and either a top or a bottom of the bluff body 23. The localized flow constrictions 22 divide the flow-through channel 21 into two chambers, a first cavitation chamber 24 having static pressure $P_1$ and a second cavitation chamber 25 having static pressure $P_2$. The second cavitation chamber 25 houses the hydrodynamic cavitation zone as discussed below. The hydrodynamic cavitation zone in the second chamber 25 has volume $V_c$.

In operation of the cavitation apparatus 20 shown in FIG. 4, liquid, such as enzymes, enters the flow-through channel 21 and flow through the localized flow constrictions 22 at a pressure and velocity such that a specified cavitation activation energy is generated wherein the hydrodynamic cavitation zone is formed and steam-filled cavitation bubbles are created. Specified range of cavitation activation energies preferably create hydrodynamic steam cavitation bubbles that collapse less energetically to avoid enzyme denaturation and deleterious effect on reactions in the alcohol production process and thereby enhance enzyme activity.

The cavitation activation energy through any of the cavitation apparatuses of FIGS. 3-4 can be calculated from the following equation:

$$\varepsilon = \frac{(P_1 - P_2) \cdot Q \cdot t}{\rho \cdot Vc}$$

wherein $\varepsilon$ (kJ/kg) is cavitational energy, $P_1$ (Pa) is the static pressure in the first chamber, $P_2$ (Pa) is the static pressure in the second cavitation chamber, Q ($m^3$/sec) is the flow rate of the liquid medium through the cavitation apparatus, t (sec) is the residence time in the hydrodynamic cavitation zone, Vc ($m^3$) is the volume of the downstream cavitation zone, and $\rho$ (kg/$m^3$) is the density of the pre-gelatinized grain-based liquid medium or pre-cavitated liquid enzyme stream.

In addition to the pressure differential created by the localized flow restriction 2 in FIG. 3 and bluff body 23 in FIG. 4, collapsing cavitation steam bubbles generate local pressure differentials and lower-energy shock waves. This additional agitation acts to greatly improve enzymes' effectiveness by significantly increasing their reaction rate without destroying the enzymes. Collapsing hydrodynamic cavitation steam bubbles under elevated static pressure can avoid generating high-temperature zones and the formation H. and OH. free radicals.

Examples of static cavitational energy sources that can be used to apply cavitational energy include, but are not limited to, static mixers, orifice plates, perforated plates, nozzles, venturis, jet mixers, eductors, cyclonettes (e.g., Fluid-Quip, Inc.), and control flow cavitation apparatuses (e.g., Arisdyne systems, Inc), such as those described in U.S. Pat. Nos. 5,810,052; 5,931,771; 5,937,906; 5,971,601; 6,012,492; 6,502,979; 6,802,639; 6,857,774 and 7,667,082. Additionally, dynamic cavitational energy sources that can be used include, but are not limited to, rotary milling devices (e.g., EdeniQ Cellunator™), rotary mixers (e.g., HydroDynamics SPR, Magellan™), rotor-rotor (e.g., Eco-Fusion Canada Inc.) and rotor-stator devices (e.g., IKA® Works, Inc., Charles Ross & Son Company, Silverson Machines, Inc., Kinematica Inc.), such as those described in U.S. Pat. Nos. 6,857,774; 7,178,975; 5,183,513; 5,184,576; 5,239,948; 5,385,298; 5,957,122; and 5,188,090.

Achieving increased alcohol yield within a particular type of cavitation process is dependent on many factors, including the location of the process at which the cavitation is applied, intensity of the cavitation, duration of time spent in hydrodynamic cavitation zone, pressure maintained in cavitation chamber, temperature, amount of enzyme and others process variables.

In order to promote a further understanding of the invention, the following Example is provided. This Example is shown by way of illustration and not limitation.

EXAMPLE

Corn flour was fed into a slurry mixer where it was mixed with hot process water. Total dry solids concentration was of 30.9% (w/w). Residence times in the slurry mixer were 30 minutes. In addition to the corn flour, a dose of α-amylase was supplied to the slurry mixer (0.016% w/w enzyme based on the weight of corn flour in the slurry mixer) such that a pre-gelatinized grain-based liquid medium was formed. Temperature, level and pH of the slurry were continuously measured using online instrumentation. Next, the pre-gelatinized grain-based liquid medium was passed from the slurry mixer to the controlled flow cavitation apparatus 10 as illustrated in FIG. 3. The pre-gelatinized grain-based liquid medium was treated by cavitation at one of two temperatures (137° F. and 170° F.) and one of four cavitation activation energies (0.00, 0.44, 0.94, and 1.56 kJ per kilogram of the pre-gelatinized grain-based liquid medium), as shown in Table 1. The pre-gelatinized grain-based liquid medium was passed through the controlled flow cavitation apparatus 10 one time as a single-pass operation. The controlled flow cavitation apparatus 10 had an orifice 3 of 5 mm. Flow rates of the pre-gelatinized grain-based liquid medium ranged from 10 to 18 gpm. Pressure in the first chamber was 100, 200 and 300 psi and static pressure in the second chamber was at least 50 psi. Duration of the pre-gelatinized grain-based liquid medium in the hydrodynamic cavitation zone was less than 0.1 second.

An aqueous grain-based material slurry that was produced after traveling through the controlled flow cavitation apparatus 10 was discharged to a portable collection tank. Samples of the aqueous grain-based material slurry were collected from the portable collection tank in 1-liter sample bottles and immediately taken to a fermentation laboratory. Once in the fermentation laboratory, an overhead agitator was used to continuously stir the samples of the aqueous grain-based material slurry to ensure that the corn solids stayed in suspension. While stirring the samples with the overhead agitator, 160 grams of the mixture was pumped from each of the 1-liter sample bottles into tarred, sterile, 250-ml Erlenmeyer flasks using a peristaltic pump. Prior to filling, the flasks were weighed to determine their total mass.

Once the aqueous grain-based material slurry was transferred to the 250-ml Erlenmeyer flasks, the 250-ml Erlenmeyer flasks were left to incubate for 1 hour at 180° F. Subsequently, the 250-ml Erlenmeyer flasks were transferred to an incubator shaker to facilitate the cooling, wherein the temperature was held to 68° F. and the 250-ml Erlenmeyer flasks were shaken at 150 rpm. After all of the 250-ml Erlenmeyer flasks were liquefied and cooled, glucoamylase, urea, and yeast nutrients were added to the 250-ml Erlenmeyer flasks. The samples were then left to ferment for at least 60 hours.

After completion of this process, total mass of each fermentation flask, including beer, was measured and compared to the initial mass of each fermentation flask. The concentration of ethanol was then measured by HPLC. Results are shown in Table 1 below.

TABLE 1

| Temperature, ° F. | Cavitation activation energy, ε kJ/kg | Enzyme concentration, % w/w | Ethanol concentration, g/100 ml | Increase ethanol yield, % |
|---|---|---|---|---|
| 170 | none | 0.016 | 13.05 | — |
| 170 | none | 0.028 | 13.09 | +0.30% |
| 170 | none | 0.040 | 13.11 | +0.45% |
| 170 | 0.44 | 0.016 | 13.11 | +0.45% |
| 170 | 0.94 | 0.016 | 13.37 | +2.45% |
| 170 | 1.56 | 0.016 | 13.44 | +2.99% |
| 137 | none | 0.016 | 13.04 | — |
| 137 | none | 0.028 | 12.91 | — |
| 137 | none | 0.040 | 12.87 | — |
| 137 | 0.44 | 0.016 | 12.95 | — |
| 137 | 0.94 | 0.016 | 13.29 | +1.92 |
| 137 | 1.56 | 0.016 | 13.23 | +1.46% |

Results from experimental data demonstrated that introduction of specified cavitation activation energy from at least 0.44 to 1.56 kJ per kilogram of grain-based or pre-gelatinized grain-based liquid medium into the pre-gelatinized grain-based liquid medium containing enzymes can improve the effectiveness of the enzymes so that the ethanol yield from grains is increased. As can be seen, a lower temperature is less effective with respect to enzyme activation. For example, a processing temperature of 137° F. generally yielded a lower increase in ethanol as compared to the results at the processing temperature of 170° F. This result is mostly likely due to the cavitation bubbles being formed at lower temperatures, which contained less steam in the cavitation bubbles and likely caused the cavitation bubbles to collapse more energetically and generate higher local pressures and temperatures. This sequence of events can promote formation of free-radicals, which can have a negative effect on the enzyme's catalytic function and explains lower relative yields.

It should now be apparent that there has been provided, in accordance with the present invention, a novel process for enhancing enzyme activity in grain-based liquid medium that satisfies the benefits and advantages set forth above. Moreover, it will be apparent to those skilled in the art that many modifications, variations, substitutions and equivalents for the features described above may be effected without departing from the spirit and scope of the invention. Accordingly, it is expressly intended that all such modifications, variations, substitutions and equivalents which fall within the spirit and scope of the invention as defined in the appended claims to be embraced thereby.

The preferred embodiments have been described, herein. It will be apparent to those skilled in the art that the above methods may incorporate changes and modifications without departing from the general scope of this invention. It is intended to include all such modifications and alterations in so far as they come within the scope of the appended claims or the equivalents thereof.

What is claimed is:

1. A process of increasing ethanol yield from grain comprising passing an enzyme through a controlled flow cavitation apparatus prior to distillation, wherein the enzyme is selected from the group consisting of alpha-amylase, glucanase, beta-glucosidases, pectinases, xylanase, amylases, ligninases, proteases, [beta]-mannosidase, and mixtures thereof and the enzyme is subjected to a cavitation activation energy in the range of 0.4 to 1.6 kJ per kilogram of liquid medium passed through the controlled flow cavitation apparatus to increase the activity of the enzyme.

2. The process of claim 1, the enzymes being subjected to a cavitation activation energy in the range of 0.6 to 1.56 kJ per kilogram of liquid medium passed through the controlled flow cavitation apparatus to increase the activity of the enzymes.

3. The process of claim 1, the cavitation activation energy is produced by static or dynamic cavitation means.

4. The process of claim 1, the enzyme being mixed with liquid prior to being passed through the controlled flow cavitation apparatus.

5. The process of claim 4, wherein no grain is passed through the controlled flow cavitation apparatus with the enzyme and the liquid.

\* \* \* \* \*